United States Patent [19]

Hakky

[11] Patent Number: 4,594,997

[45] Date of Patent: Jun. 17, 1986

[54] SELF ACTUATED PENILE IMPLANT

[76] Inventor: Said I. Hakky, 185 Dagenham Road, Rush Green, Romford, Essex RM7 OTL, England

[21] Appl. No.: 670,832

[22] Filed: Nov. 13, 1984

[51] Int. Cl.⁴ .............................................. A61F 5/00
[52] U.S. Cl. ........................................ 128/79; 623/11
[58] Field of Search ....................... 128/79; 623/11, 12

[56] References Cited

U.S. PATENT DOCUMENTS

| | | | |
|---|---|---|---|
| 3,954,102 | 5/1976 | Buuck | 128/79 |
| 4,009,711 | 3/1977 | Uson | 128/79 |
| 4,267,829 | 5/1981 | Burton et al. | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,369,771 | 1/1983 | Trick | 128/79 |
| 4,378,792 | 4/1983 | Finney | 128/79 |
| 4,383,525 | 5/1983 | Scott et al. | 128/79 |
| 4,399,811 | 8/1983 | Finney et al. | 128/79 |
| 4,468,220 | 8/1984 | Willbanks | 604/890 X |
| 4,498,466 | 2/1985 | Pomeranz | 604/349 |

Primary Examiner—Stephen C. Pellegrino
Attorney, Agent, or Firm—Caesar, Rivise, Bernstein & Cohen, Ltd.

[57] ABSTRACT

A self-activatable penile prosthesis comprising at least one cylinder for implantation in the penis and including a front tip section, an intermediate section, and a rear tail section. The intermediate section includes at least one tubular member which is inflatable, and arranged to assume an elongated rigid and hard state from a flexible, flaccid state upon the application of an operating liquid under pressure thereto. An expandable bellows having an actuating fluid therein is located in the tip section. The actuating fluid expands from a first state to a second higher volume state upon the application of energy (e.g., heat) thereto. The expansion action causes an operating liquid located in at least one reservoir in the tip section to be provided under pressure to the inflatable tubular member in the intermediate section to cause it to become erect. Upon the dissipation of said energy from the actuating fluid the bellows contracts, whereupon the intermediate section of the cylinder becomes flaccid again.

35 Claims, 15 Drawing Figures

SELF ACTUATED PENILE IMPLANT

BACKGROUND OF THE INVENTION

This invention relates generally to implantable penile prostheses and more particularly to implantable, self-actuated penile prostheses.

Various penile implants have been disclosed in the patent literature and are commercially available for curing erectile impotence. Such devices basically comprise a pair of cylinders each of which adapted to be implanted in a respective corpus cavernosum of the penis. Each cylinder includes a hollow portion arranged to be pressurized by the pumping of a liquid therein. When the cylinder portions are pressurized the penis assumes an erect, rigid state. The liquid used to inflate the cylinders is provided via respective tubes from a liquid supply reservoir. A pump and a reversible, one-way valve, are also included in the prosthesis and are typically arranged to be implanted in the scrotum and/or the abdomen. The pump and valve enable the liquid to be carried from the reservoir into the cylinder to cause the erection when the valve is in a first setting. In order to render the penis flaccid the valve is arranged to be actuated to enable the liquid to pass through it in the opposite direction so that operation of the pump carries the liquid back into the reservoir.

Examples of penile implants utilizing the foregoing technology are shown in U.S. Pat. Nos. 3,954,102 (Buuck), 4,009,711 (Uson), 4,267,829 (Burton et al), and 4,342,308 (Trick). While the foregoing pump-type inflatable penile implants all operate on the same basic principle each of those devices include some different structural features, e.g., reinforcing or constraining materials surrounding the inflatable chamber, cylinders including rigid (solid) tip and tail portions, special actuating valves, etc., all in the interest of providing a device which will closely simulate a natural erection, is easy to operate, and which exhibits a long service life.

While the penile implants such as described above have proven suitable for their intended purposes, they nevertheless leave something to be desired from the standpoint of simplicity of construction and ease of operation. In this regard all of the above identified prior art implants require the use of not only the inflatable cylinders which are to be located within the penis, but also a control valve, pump and reservoir, all of which are implanted within the body remote from the penis. Moreover, operation of such remotely located pump-type penile implants requires the user to first manually operate the valve to its appropriate setting to enable flow from the reservoir to the cylinders and then to manually pump the liquid into cylinders to cause the penis to become erect for sexual intercourse. In order to render the penis flaccid the valve has to be manually returned to its initial position to enable the liquid to flow therethrough in the opposite direction so that operation of the pump carries the liquid from the cylinders back into the reservoir.

Another type of penile prosthesis has been disclosed in various patents. That alternative penile prosthesis constitutes a variation of the externally located pump-type device. In this regard the alternative type penile implant utilizes a pump and reservoir which are both located within the cylinder, with the pump in either the tip portion or an intermediate portion and with the reservoir located within the intermediate or rear portion. Thus the entire prosthesis is self-contained within the cylinder and does not require the use of remotely located reservoirs/valves/pumps. Operation of such a self contained type of penile prosthesis is effected by squeezing the portion of the cylinder containing the pump to operate it to cause liquid to flow from the reservoir into an inflatable chamber located at an intermediate point in the cylinder to cause the cylinder to become erect. While this type of penile implant offers the advantage of simplicity of construction over remotely located pump-type implants, it still leaves something to be desired from the standpoint of functionality and ease of operation. Examples of the self contained penile prosthesis are shown in U.S. Pat. Nos. 4,353,360 (Finney et al), 4,360,010 (Finney), 4,369,771 (Trick), and 4,399,811 (Finney et al).

Other types of prior art penile prostheses are shown in U.S. Pat. Nos. 4,378,792 (Finney) and 4,383,525 (Burton et al).

OBJECTS OF THE INVENTION

Accordingly, it is the general object of the instant invention to provide a penile implant which overcomes the disadvantages of the prior art.

It is a further object of the instant invention to provide a penile implant which more naturally simulates the production of an erection.

It is a further object of the instant invention to provide a penile prosthesis which is readily adapted to assume an erect rigid state and to remain in that state upon the application of energy to said prosthesis.

It is a further object of the instant invention to provide a penile prosthesis which assumes a erect rigid state upon the application of energy thereto, remains in said erect state so long as said energy is applied, and thereafter assumes a non-erect flaccid state after the dissipation of such energy.

It is a further object of the instant invention to provide a penile prosthesis which includes a fluid which is arranged to expand upon the application of energy thereto to cause said penile implant to become erect.

It is still a further object of the instant invention to provide a completely self-contained implantable penile prosthesis.

SUMMARY OF THE INVENTION

The prosthesis comprises a cylinder adapted for implantation in the penis and includes means for automatically causing a portion of the cylinder to move from a non-erect, flaccid state to an erect, rigid state and to remain in that state upon the application of energy thereto. The cylinder portion automatically reverts to the flaccid state after the energy has dissipated.

DESCRIPTION OF THE DRAWING

Other objects and many of the attendant advantages of the instant invention will be readily appreciated when the same becomes better understood by reference to the following detailed description when considered in connection with the accompanying drawing wherein.

DETAILED DESCRIPTION OF THE PREFERRED EMBODIMENT

Referring now in greater detail to the various figures of the drawing wherein like reference characters refer to like parts, there is shown an implantable penile prosthesis 20 constructed in accordance with the subject invention. The prosthesis 20 basically comprises an elongated cylindrical member 22 having a substantially rigid front or tip section 24, a substantially rigid rear or tail section 26 and an inflatable intermediate section 28. In normal practice two such cylinders 22 are utilized to make up a complete penile prosthesis. In such a case each cylinder is surgically implanted longitudinally in a respective corpus cavernosum (not shown) of the penis, with the tip section 24 located within the distal portion of the penis and with the tail section 26 located within the proximal portion of penis. The tip section 24 is formed of a mass or body of an elastomeric material, such as medical grade silicone rubber, so that it is substantially rigid. The body of the tip section includes a hollow portion in which various components (to be described later) are located. The inflatable intermediate section is a generally hollow member having an outer wall formed as a thin sleeve of an elastomeric material, such as a medical grade silicone rubber, and including expandable components (to be described later) located therein. The intermediate section is thus constructed to be flexible and flaccid in its normal or unactivated state, but is arranged to be expanded linearly but not radially and made rigid when the prosthesis is activated to render the penis erect. In such a case the three sections making up the cylinder of the prosthesis act like a cantilevered beam, with rear section 26 serving to anchor the intermediate and tip sections of the prosthesis to the body.

As will be fully appreciated from the description to follow the device 20 of the subject invention is a completely self-contained unit and does not require the use of remotely implanted reservoir/valve/pump arrangements for causing the device to become erect. Thus, the prosthesis 20 includes within each cylinder 22 itself the actuating means for causing the penis to become erect and for allowing the penis to become flaccid when the erection is no longer desired. Moreover, and quite significantly, the subject prosthesis does not require the use of a manually actuatable pump (whether implanted remotely of the cylinder or included within the cylinder itself) to cause the prosthesis to become erect. In this regard the means for effecting the erection of the prosthesis 20 operates in automatic response to the application of energy to the prosthesis. Thus, when energy is applied the prosthesis becomes erect and remains erect, yet when the energy is removed and dissipated the prosthesis becomes flaccid. This feature enables the prosthesis 20 to be somewhat automatic in operation, thereby closely simulating the natural erection process.

Figure 1:
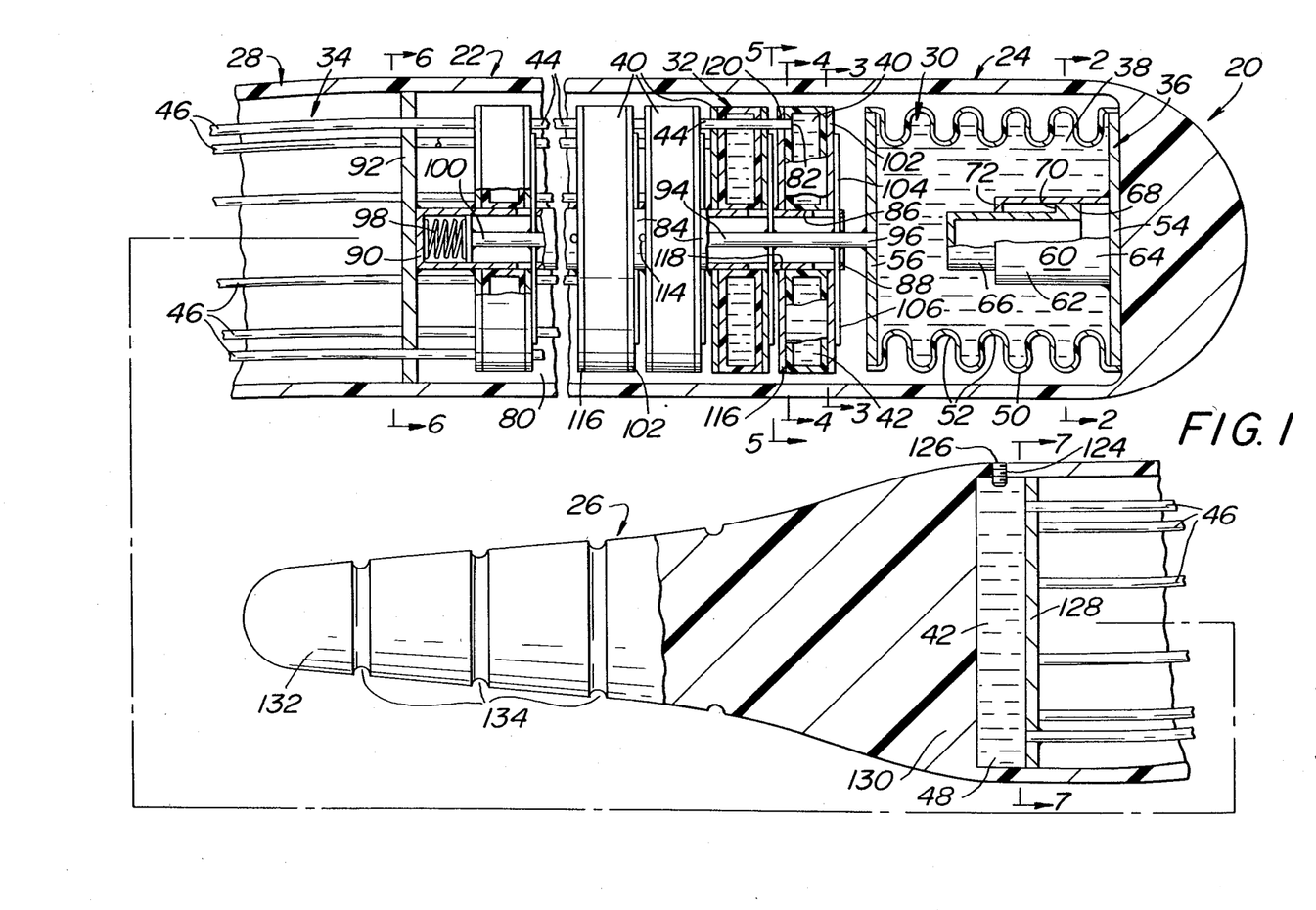
FIG. 1 is a side elevational view, partial broken away, showing one cylinder of a prosthesis constructed in accordance with this invention in its flaccid state.

As shown clearly in FIG. 1 the basic functional components of the prosthesis 20 are an expansion chamber assembly 30, a fluid reservoir assembly 32, and an inflatable assembly 34, all of which are located within the cylinder 22. The expansion chamber assembly will be described in detail later. Suffice for now to state that the expansion chamber assembly includes an enclosed, hollow, expandable bellows member 36. The bellows member is located within a hollow portion of the tip section 24 and contains an actuating fluid 38 therein. The actuating fluid serves as the means for causing the prosthesis to become erect or flaccid, as the case may be. In this regard the actuating fluid is arranged to change from the first physical state to a second state having a higher volume than the first state when its temperature is increased beyond a predetermined threshold temperature and to return to the first state when its temperature is at or below that threshold temperature. It must be noted at this juncture that the second state may or may not be the same phase, e.g., liquid or gas, as the first state, so long as it is of a higher volume. The increasing of the temperature of the fluid 38 to operate the prosthesis is effected by the application of energy, e.g., heat, to the fluid as will be described later. As should be appreciated by those skilled in the art when the actuating fluid 38 is in the second (higher) volumetric state the bellows member 36 expands.

As can be seen in FIG. 1, there is also located within the hollow portion of tip section 24 of the cylinder 22, but to the rear of the expansion bellows member 36, the reservoir assembly 32. That assembly will be described in detail later. Suffice for now to state that the reservoir assembly is composed of plural, individual, sealed-reservoir chambers 40, each containing an operating liquid 42, e.g., saline solution, therein. The operating liquid serves as the means for inflating the inflation assembly 34 to produce the erection. Each reservoir chamber 40 includes an outlet passageway or conduit 44. Each conduit is a rigid tubular member which extends toward the rear of the prosthesis into the intermediate section 28 for communication with the inflatable assembly 34 located therein.

Figure 8:
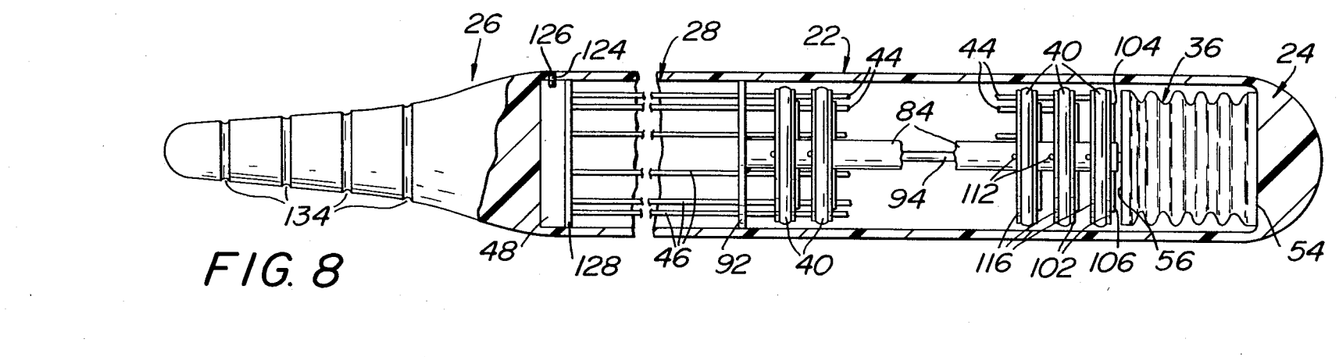
FIG. 8 is a view similar to that of FIG. 1 but showing the cylinder in its erect state.

The inflatable assembly 34 will also be described in detail later and basically comprises a plurality of flexible, elastomeric tubes 46. The tubes 46 lie in a side-by-side array and extend the length of the hollow interior of the intermediate section 28 of the prosthesis. The forward end of each tube 46 joins to and is in fluid communication with a respective rigid conduit 44 connected to an associated reservoir chamber 40. The inflatable tubes 46 are arranged such that when the prosthesis is in its flaccid state, the tubes contain some operating liquid, but that liquid is not under pressure so that the tubes are limp and flaccid, like shown in FIG. 1. However, when the operating liquid 42 is pressurized by the constriction of the reservoir chambers, an action caused by the expansion of the bellows member 36 and which will be described in considerable detail later, additional operating liquid is forced into the tubes, whereupon they expand longitudinally but not radially from their limp or flaccid state to an erect and generally linear, rigid state like that shown in FIG. 8. The elongation and stiffening of the plural tubes 46 causes the intermediate section 28 of the prosthesis to elongate and stiffen, thereby moving the three sections 24, 28 and 26 of the cylinder into general axial alignment like shown in FIG. 8, whereupon the penis is rendered erect and hard. The prosthesis maintains this state of erection so long as the fluid 38 within the bellows member 36 is in the second (higher) volume phase.

In accordance with the preferred embodiment of this invention the fluid utilized in the expansion chamber means is selected so that in the normal quiescent temperature state, that is, under normal core body temperature, i.e., 38° C., and mechanically stable conditions, as exist in normal in day-to-day, non-sexual activities, the fluid is in the first lower volume state. When the temperature of the fluid rises above the threshhold level, e.g., 38° C., such as by the application of heat or mechanical energy, e.g., upward and downward motion of the prosthesis to be described later, the fluid's volume expands to the higher volume, second state. The volume of the fluid does not decrease back to the first volume until its temperature again decreases below the threshold level.

Any suitable actuating fluid can be used providing it exhibits low toxicity and sufficient thermal-expansion/-contraction characteristics to operate the bellows to produce sufficient pressure to render the inflatable assembly in the intermediate section rigid. Among those fluids which appear suitable for use in the prosthesis of this invention are those polyhalogenated derivatives of methane and ethane containing fluorine (and in most cases chlorine or bromine) which are referred to as the freons. As is known the freons possess the characteristics of non-flammability, excellent chemical and thermal stability, low toxicity, high density, low boiling point, low viscosity, and low surface tension. Of the commonly available freons the following appear particularly suitable for use as the actuating fluid for this invention: trichlorofluoromethane, dichlorodifluoromethane, chlorodifluoromethane, and dichlorotetrafluoroethane, designated by the trademarks FREON-11, FREON-12, FREON-22 and FREON 114, respectively, of E.I. DuPont de Nemours and Company. As is known fo those skilled in the art of the four fluorcarbon fluids 38 described above FREON 22 exerts the highest pressure upon expansion, FREON 114 exerts the least pressure, and FREON 11 and FREON 12 exert an intermediate pressure. It is the pressure produced by the expansion of the fluid 38 which causes the bellows member 36 to expand in its longitudinal direction, to be described later.

The penile prosthesis 20 is constructed so that all that is required to produce an erection prior to sexual intercourse is for the person to gently move or shake his penis a few times upwardly and downwardly. This action supplies sufficient mechanical energy to means (which will be described later) in the bellows member to raise the temperature of the actuating fluid 38 and thereby cause it to expand to its higher volume state, whereupon the reservoir chambers 40 are constricted or compressed. Such action causes additional operating liquid to flow under pressure through the rigid conduits 44 into the flexible tubes 46 of the intermediate section, whereupon that section assumes its rigid, erect state. Moreover, as will also be described later, the thrusting action of the penis during sexual intercourse, coupled with the heat generated at the penis during intercourse, provides additional energy to the actuating fluid in the prosthesis to maintain it in it higher volume state, thereby automatically maintaining the erection. Upon the cessation of intercourse the removal of the application of physical energy and heat to the prosthesis enables the actuating fluid within the prosthesis to cool down below its threshold level, whereupon it returns to its lower volume first state.

As will be described later bias means are coupled to the bellows member 36 to enable it to contract when the fluid therein decreases in volume to its first phase. This action allows some of the liquid in the flexible tubes to flow back into the reservoir chambers 40, whereupon the pressure in the flexible tubes 46 decreases so that cylinder section 28 again becomes flaccid.

Figure 2:
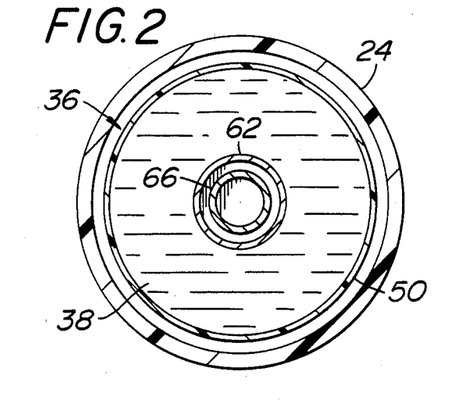
FIG. 2 is a sectional view taken along line 2—2 of FIG. 1.

Referring now to FIGS. 1 and 2 the details of the bellows member 36 will now be described. That member basically comprises a bellows element formed as a hollow, enclosed or sealed body having a circular side wall 50. The circular side wall includes plural convolutions 52 therein. The side wall is formed of a strong and lightweight material which is suitable for repeated expansion and contraction without failure and which will not deleteriously be affected by the composition of the actuating fluid 38. In this regard and in accordance with the preferred embodiment of this invention the bellows wall 50 is formed of a very thin, e.g., 0.03 mm, metal, such as pure commercial grade titanium. Other available metals, such as nickel, may also be used. The bellows member 36 also includes a rigid front wall 54 and a rigid rear wall 56, both also formed of the same material as the bellow's side wall. The front wall 54 is fixedly secured to the body of material forming the tip section to hold the bellows member at a fixed position within the tip section.

The bellows member is rather small in size, e.g., approximately 9.3 mm in diameter and 2-2.5 cm long. The bellows is arranged to expand longitudinally, that is the spacing between the front wall 54 and the rear wall 56 is arranged to increase, e.g., approximately 5 mm, when the fluid 38 expands from its first volumetric phase to its second volumetric phase.

In order to provide energy in the form of heat to the fluid 38 when an erection is desired, the bellows member 36 includes friction-operated, heat-generating means 60. The heat-generating means 60 consists of an outer collar 62 of tubular construction and whose front end 64 is fixedly secured to the front wall 54 of the bellows member 36. In the preferred embodiment of the invention, the outer collar is 5 mm in diameter and 12 mm in length. Disposed within the outer collar 62 is an inner collar 66 also of tubular construction. In the preferred embodiment the inner collar is 4 mm in diameter and 10 mm in length. The inner collar is arranged to reciprocate longitudinally with respect to the outer collar from a retracted position (like shown in FIG. 9b) wherein it is almost fully retracted within the outer collar, to an extended position (like shown in FIG. 9a)

wherein it is almost fully extended out of the outer collar, and vice versa.

As can be seen clearly in FIG. 2 the forward end 68 of the inner collar 66 includes catch means 70 which cooperates with means 72 on the outer collar to prevent the inner collar from being extended completely out of the outer collar.

The outside diameter of the inner collar is chosen to be sufficiently close, e.g., 1 mm smaller, to the inside diameter of the outer collar so that inner collar frictionally engages or rubs against the outer collar yet readily reciprocates therein. Moreover each collar is formed of a good thermally transmissive material, e.g., metal. The reciprocation action of the inner collar with respect to the outer collar results in the creation of friction therebetween. That friction induces heat in the collars, which heat is efficiently transferred by the thermally transmissive material making up the collars to the surrounding actuating fluid. The heat supplied to the fluid causes the fluid to expand from its quiescent first volumetric state to its larger volume, second state. As can be seen in FIG. 1 the length of the two collars 62 and 66 is such that when the collars are in the extended position their combined length is less than the length of the interior of the bellows member 36 when it is in its contracted (shorter) state so the bellows does not interfere with the reciprocation action of the collars.

Figure 9A:
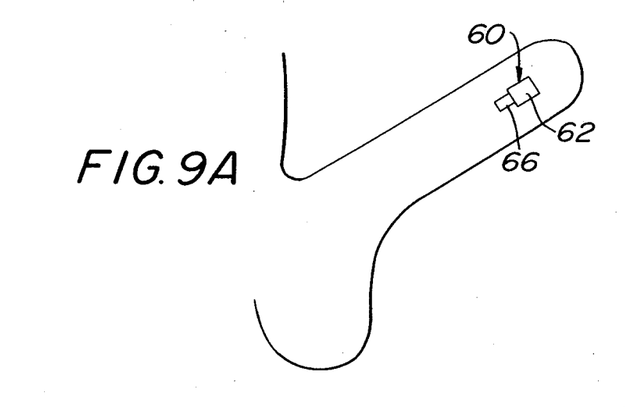
FIGS. 9A and 9B are diagramatic side elevational views of a penis oriented slightly upward and downward, respectively, shown exaggerated to demonstrate the opertion of energy generating means in the prosthesis.
Figure 9B:
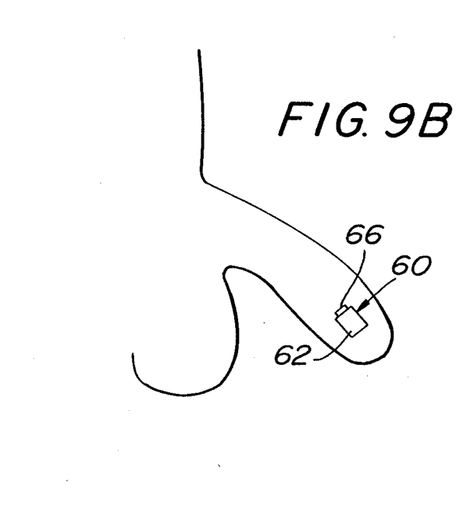

With the collars arranged as described heretofore all that is necessary to create an erection prior to intercourse is for the patient to move his penis upward toward the abdomen and then downward the thigh several times like shown in FIGS. 9a and 9b. This action causes the inner collar to reciprocate with respect to the outer collar as a result of the combined effects of gravity and inertia. As stated earlier this reciprocation generates heat in collars which transmit that heat to the surrounding actuating fluid, thereby causing the fluid in the bellows to expand. Moreover since the bellows member 36 is fully enclosed within the tip portion of the prosthesis (which portion is preferably formed of an elastomeric material, such as medical grade silicone rubber), the body of the tip portion acts as a good thermal insulator so that heat in the actuating fluid dissipates very slowly from the bellows.

Moreover, since the direction of the vagina is always in an upward and backward orientation during the most common positions assumed by the female partner in sexual intercourse the penis will normally point in an upward and forward orientation when it is within the vagina. In this orientation the inner collar telescopes out of the outer collar due to the action of gravity. Moreover, each time the penis is slightly withdrawn from the vagina during intercourse, the inner collar retracts inside the outer collar due to the inertia of the inner collar. Accordingly, during sexual intercourse the to-and-fro movement of the penis is transmitted to the inner collar, thus causing its reciprocation into and out of the outer collar. Such action results in further friction-induced heat being provided to the surrounding actuating fluid.

The details of the fluid reservoir assembly will now be described. That assembly basically comprises the heretofore identified chambers 40 as well as means for constricting or compressing them. Those components can best be seen by reference to FIGS. 1, 3, 4 and 5. Thus, as can be seen therein each reservoir chamber 40 is in the form of a hollow annulus. Each annulus is of thin-walled construction formed of medical grade silicone rubber and is approximately 10 mm in diameter and 5 mm in length, with a volumetric capacity of approximately 0.4 ml.

In accordance with the preferred embodiment of the invention at least four reservoir chambers 40 are utilized in the prosthesis. Those chambers are disposed at equadistantly spaced longitudinal positions to the rear of the bellows in a cylindrical cavity or compartment 80 located in the tip section of the prosthesis. Each reservoir chamber includes an outlet opening 82 fixedly connected to and in fluid communication with a respective rigid conduit 44 to enable the operating fluid 42 to flow into and out of it.

An elongated, linear, hollow shaft 84 extends through the central opening 86 in each of the reservoir chambers 40 and includes a front end 88 located adjacent but spaced from the rigid rear wall 56 of the bellows member 36. The rear end 90 of the shaft is closed and is disposed closely adjacent the intermediate section 28 of the prosthesis. The shaft 84 is held firmly in place against movement within the tip section of the prosthesis by being anchored at its rear end in a transverse wall 92 forming the rear end of the tip portion 24 of the prosthesis. An elongated rod 94 of approximately 1 mm outside diameter (just slightly smaller than the inside diameter of the shaft 84) is located within shaft 84. The rod 94 extends substantially the full length of the hollow shaft 84 and is fixedly secured at its front end 96 to the rear wall 56 of the bellows member 36. A helical compression spring 98 is disposed within the tubular shaft 84 and interposed between the rear end 90 of the shaft and the rear end 100 of the rod 94. The rod 94 is arranged to be moved longitudinally toward the rear of the prosthesis by the expansion of the fluid in the bellows member 36 and to be moved longitudinally toward the tip of the prosthesis under the bias force of the spring 98 when the fluid inside the bellows member contracts.

Figure 3:
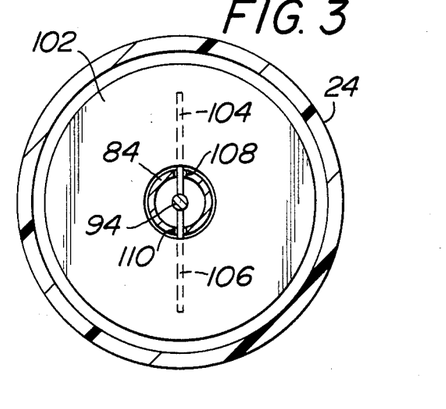
FIG. 3 is a sectional view taken along line 3—3 of FIG. 1.
Figure 4:
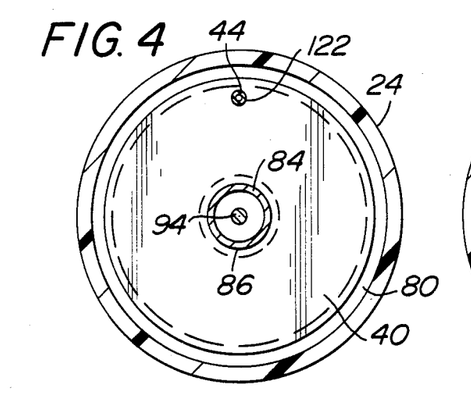
FIG. 4 is a sectional view taken along line 4—4 of FIG. 1.
Figure 5:
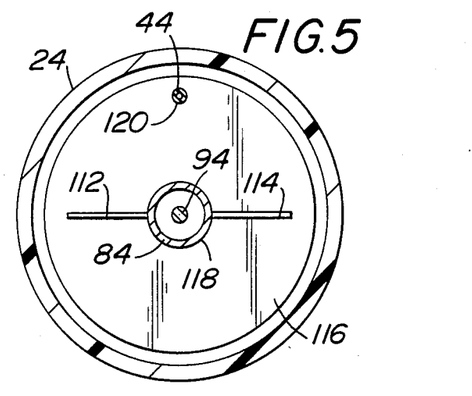
FIG. 5 is a sectional view taken along line 5—5 of FIG. 1.

As can be seen clearly in FIGS. 1, 3 and 5 a plurality of planar disks 102 are located at fixed longitudinally equadistantly spaced locations along shaft 84. Each disk is of generally circular profile and includes a central opening through which the shaft 84 extends. Plural opposed pairs of vertically oriented support ribs 104 and 106 project outward radially from the shaft 84 and are fixedly secured to the shaft. Each pair of ribs is fixedly secured to the associated disk to stationarily mount the disk on the shaft at the proper longitudinal position. The shaft 84 also includes a plurality of pairs of elongated slots 108 and 110 therein. The pairs of slots are located at longitudinally equadistantly spaced locations along the shaft 84 between the disks 102 and located intermediately the ribs 104 and 106. Moreover the slots 108 and 110 making up each pair are disposed diametrically from each other.

Plural opposed pairs of horizontally oriented support ribs 112 and 114 project outwardly from the moveable rod 94 and are fixedly secured thereto at longitudinally equadistantly spaced locations so that each rib 112 extends through an associated slot 108 and each rib 114 extends through an associated slot 110. A respective planar disk 116 is fixedly secured to each pair of ribs 112 and 114. Each disk 116 is similar to each disk 102 and includes a central opening 118 through which the shaft 84 freely passes.

Each of the annular reservoir chambers 40 is disposed within a respective space between immediately adjacent disks 102 and 116 within the compartment 80 in the tip section. Moreover each of the rigid conduits 44 which are connected to the respective reservoir chambers 40 extends through aligned openings 120 in the disks 102 and 116 and through openings 122 in the reservoir chambers 40, respectively.

Figure 6:
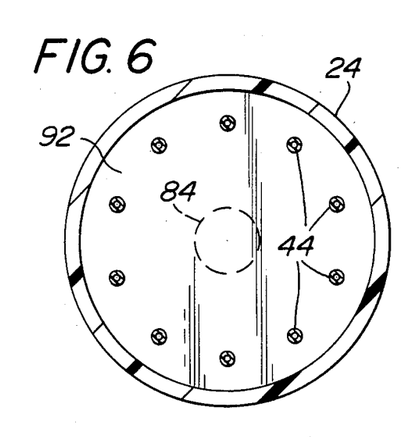
FIG. 6 is a sectional view taken along line 6—6 of FIG. 1.

The details of the tubes 46 making up the inflatible means 34 of the intermediate section can best be seen by reference to FIGS. 1 and 6. As can be seen therein, each tube 46 is an elongated member formed of a resilient material which is arranged and reinforced so that when provided with the operating liquid under pressure it expands only longitudinally while becoming rigid and hard. As stated earlier each tube 46 is in communication at its front end with an associated rigid conduit 44 from the associated reservoir 40 and is also in communication at its rear end in a common, enclosed filling chamber 48. The chamber 48 is formed by a small recess located in the rear or tail section 26 of the prosthesis and closed off by a front wall 128. The operating saline solution 42 for the prosthesis is introduced into the chamber 48 during the surgery implanting the prosthesis via a radially extending orifice 124 in the side of the tail section. Once the implant is filled with the operating fluid a screw cap 126 is disposed in the orifice 124 to seal the operating fluid within the prosthesis.

As will be appreciated by those skilled in the art from the foregoing the expansion of the bellows member 36 causes the rearward movement of rod 94, thereby causing each of the attached disks 116 to move to the rear. This action constricts or compresses each reservoir chamber 40 between the associated moving disk 116 and the associated fixed disk 102, whereupon the operating liquid in each reservoir chamber is forced under pressure through the associated rigid tube 44 into the associated inflatible tube 46. With the large number, e.g., 5, of reservoirs used in the prosthesis, even a small displacement of 5 mm of the bellows to the rear causes a total of approximately 1.5-2 ml of liquid to be provided into the tubes 46. Such action provides sufficient liquid under sufficient pressure to the flexible tubes 46 to cause them to assume a very rigid, linear and expanded state, thereby rendering the intermediate section 38 of the prosthesis rigid and hard.

Figure 7:
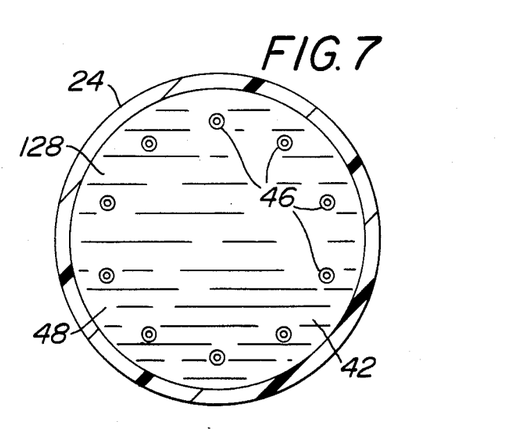
FIG. 7 is a sectional view taken along line 7—7 of FIG. 1.

As can be seen clearly in FIG. 7 the tail section 26 of the prosthesis basically comprises a solid body, also preferably formed of a medical grade silicone rubber, and having a cylindrical front portion 130 and a tapering rear portion 132. The filling chamber 48 is located in the front end of the front portion 130 of the tail section.

A plurality of longitudinally spaced, annular recesses 134 are provided in the surface of the rear portion 132 of the tail section. These recesses serve as convenient locations for severing a portion of the rear section away from the remainder of the cylinder 22 to configure the prosthesis to the appropriate size for the penis into which it will be implanted.

In FIGS. 10-14 there is shown an alternative embodiment 200 of the prosthesis of this invention. The prosthesis 200 includes many of the same components as described heretofore and such components are thus given the same reference numerals.

In prosthesis 200 the heretofore described fluid reservoir assembly 32 and the inflatable assembly 34 are replaced with different components for effecting similar functions. In this regard the prosthesis includes a piston operated fluid reservoir assembly 202 and an inflatable chamber 204 located within cylinder 22.

The chamber 204 comprises a tubular body extending the length of the intermediate section 28. The tubular body is formed of a resilient, yet non-distendable material, such as a medical grade silicone rubber reinforced with a woven Dacron mesh. The rear end 206 of the inflatable chamber 204 is closed while its front end is open at 208. In a preferred embodiment the chamber is approximately 10 mm in diameter and 7 cm long.

The fluid reservoir assembly 202 basically comprises a tubular body formed of a rigid plastic and having a circular sidewall 212 extending a substantial length of said tip section 24 and located between the bellows 38 and the inflatable chamber 204. The body includes an intermediate wall 214 perpendicularly oriented with respect to the sidewall 212 and having a central opening 216 in the form of a longitudinally extending tube 218. In a preferred embodiment the tube is approximately 25 mm long.

The intermediate wall 214 and the circular sidewall 212 define a front chamber 220 and a rear chamber 222, the latter serving as the operating fluid reservoir of the prosthesis. A moveable piston 224 is located within the front chamber at the front end 226 thereof. The piston 224 includes a piston head 228 of generally conical shape and formed of a resilient material, e.g., neoprene rubber. The piston 224 is fixedly mounted on the rear wall 56 of the bellows 38 so that it moves longitudinally down the chamber 220 when the bellows expands and moves up the chamber when the bellows contracts.

The front chamber is of a diameter (e.g., 9 mm) which is substantially close to the diameter of the cylinder 22 and is of a relatively short length (e.g., 5 mm) whereupon its volume capacity is 0.39 ml and is filled with a suitable hydraulic fluid, e.g., a silicone liquid such as type DC 550 sold by Dow Corning.

The fluid reservoir assembly 202 also includes a second moveable piston 230. To that end the piston 230 includes an elongated piston shaft 232 extending the length of tube 218 so that its free end 234 is located at the outlet of hydraulic chamber 220. The piston 230 also includes a piston head 236 which is fixedly mounted at the opposite end of the shaft and within the reservoir 222. The piston head 236 includes a circular sidewall portion 238 extending back over the tube 218 toward the intermediate wall 214 and terminating in a radially extending flanged portion 240 located immediately adjacent the intermediate wall. A ring-like resilient sealing gasket 242 is disposed about the free end of the piston shaft 232 and located within an annular recess 244 therein. The gasket prevents the leakage of hydraulic fluid from the chamber 220 into the interface between the surface of the piston rod 232 and the tube 218.

As can be seen the reservoir 222 is an annularly shaped hollow member defined between the sidewall 212, the intermediate wall 214 and the tube 218. The rear end of the reservoir 222 is open and connected to and in fluid communication with the open end 208 of the inflatable chamber 204. The chamber 222 is filled with the operating fluid 42, in this case the same type of silicone liquid as in chamber 220.

The piston head 236 is located within the reservoir 222 and is arranged to be moved down the reservoir in automatic response to the movement of the first piston 224. That action occurs as follows: when the bellows 36 expands, as described heretofore, the piston 224 is moved from the position shown in FIG. 10 down the short length of the chamber 220 to the position shown in FIG. 12. This action forces the hydraulic liquid out of the chamber and against the free end of the piston 230. The volumetric capacity of the interior of the tube 218 is slightly less than or equal to the capacity of the hydraulic chamber 220 but its diameter is substantially less, e.g., 3–4 mm, thus the piston 230 moves down tube 218 a much greater distance, e.g., 25 mm, than the distance that piston 224 moves, whereupon a substantially great volume, e.g., 1.5 ml, of operating fluid 42 located in reservoir 222 is forced into the inflatable chamber 204. This action causes that chamber to move from a non-erect, flaccid state like that shown in FIG. 10, to an erect, rigid and linear state like that shown in FIG. 12.

Figure 10:
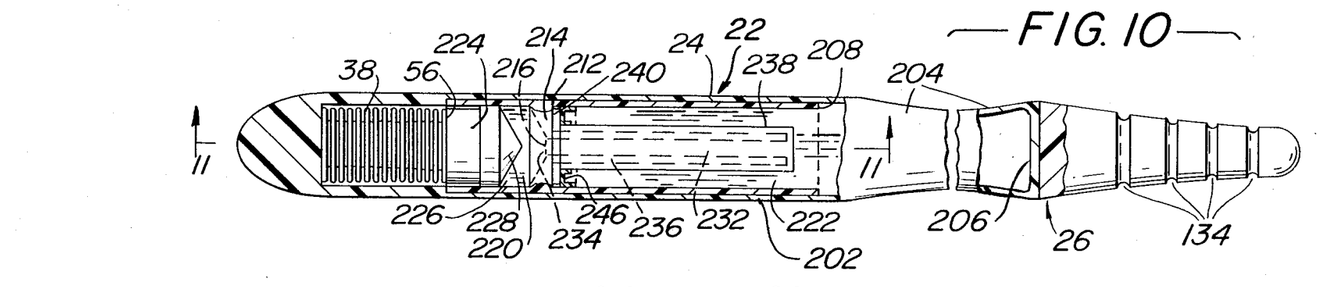
FIG. 10 is a side elevational view, partially in section, of an alternative embodiment of this invention shown in its flaccid state.
Figures 11, 14:
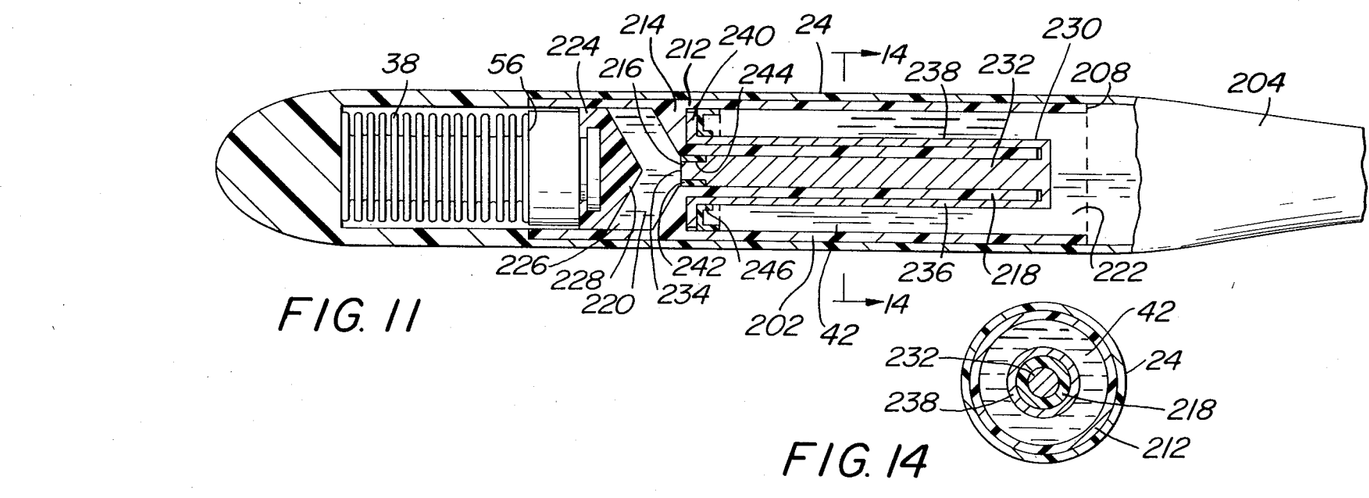
FIG. 11 is an enlarged sectional view, taken along line 11—11 of FIG. 10.
FIG. 14 is a sectional view taken along line 14—14 of FIG. 11.
Figures 12, 13:
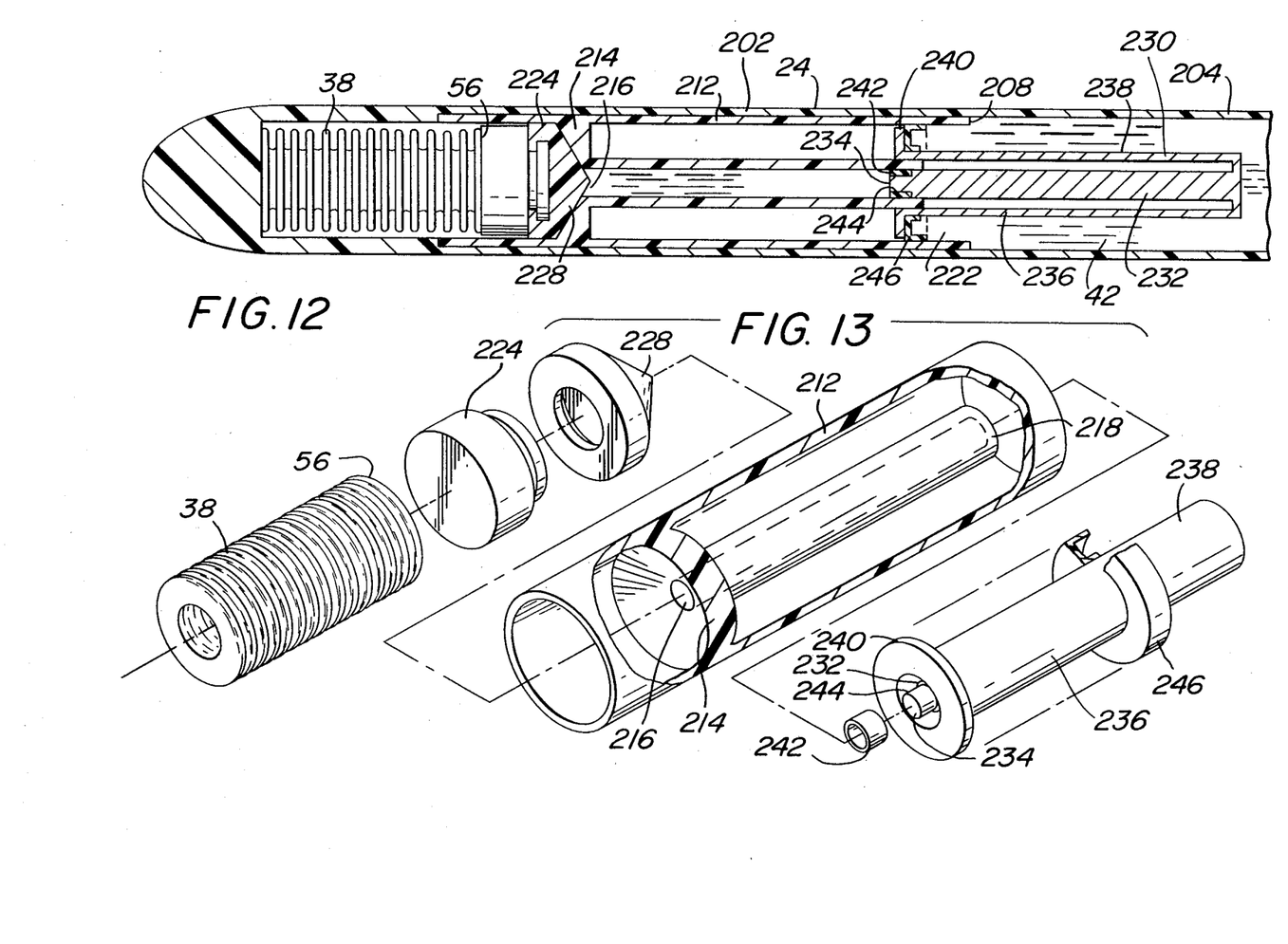
FIG. 12 is a view similar to that of FIG. 11 but showing the prosthesis in its erect state.
FIG. 13 is an exploded isometric view of a portion of the interior of the embodiment of the invention shown in FIGS. 10 and 12.

When the bellows 36 contracts the front end piston 224 is moved toward the tip of the prosthesis again, whereupon hydraulic chamber 220 again refills with the hydraulic fluid, so that piston 234 again moves to the front of reservoir 222 and the reservoir again fills with operating liquid, thus depressurizing the inflatable chamber 204 and causing the intermediate section 28 of the prosthesis to become flaccid once again (i.e., assume the position shown in FIG. 10).

In order to preclude the egress of the operating fluid between the piston head 236 and the circular side wall 212 a second, ring-like resilient sealing gasket 246 is employed. That gasket is mounted on the flanged portion 240 of the piston head.

As will be appreciated from the foregoing the device of the instant invention is self-activating and hence almost automatic in operation to closely approximate a natural erection. Moreover the device is simple in construction and does not require as extensive a surgical procedure for its implantation as does conventional penile implants due to the latter's use of remotely located pumps/valves/reservoirs.

Without further elaboration, the foregoing will so fully illustrate my invention that others may, by applying the current or future knowledge, readily adopt the same for use under various conditions of service.

I claim:

1. An implantable penile prosthesis comprising an elongated cylinder for disposition within the penis, said cylinder including a first portion adapted to move from a non-erect, flaccid state to an erect, rigid state, said prosthesis comprising actuating means including expandable means with a first fluid therein and energy applying means, said first fluid being in a first state occupying a first volume when said expandable means is unexpanded, said first fluid being changed to a second state capable of occupying a second volume greater than said first volume upon the application of energy thereto by said energy applying means for expanding said expandable means and causing said first portion of said cylinder to move to said rigid state, said fluid returning to its first state upon dissipation of said energy for causing said expandable means to return to its unexpanded condition and thereby cause said first portion of said cylinder to return to said non-erect, flaccid state, said energy applying means being operative for applying energy to said first fluid when an erection of said penis is desired and for ceasing to apply energy to said first fluid when it is desired to permit the penis to assume a non-erect, flaccid state.

2. The prosthesis of claim 1, wherein said actuating means additionally comprises inflatable means responsive to said expandable means and which is adapted to be pressurized when said expandable means is expanded to cause said cylinder to become erect.

3. The prosthesis of claim 2, wherein said inflatable means includes wall means defining an opening, said opening being adapted to be provided with a second fluid under pressure when said expandable means is expanded.

4. The prosthesis of claim 3, wherein said inflatable means comprises at least one tube located within and extending longitudinally through said first portion of said cylinder.

5. The prosthesis of claim 4, additionally comprising at least one fluid reservoir located adjacent said expandable means within a front portion of said cylinder for providing said second fluid to said tube.

6. The prosthesis of claim 5, wherein said inflatable means comprises plural tubes located within and extending longitudinally through said first portion of said cylinder and wherein plural reservoirs are disposed longitudinally in said cylinder and arranged to be compressed when said expandable means is expanded size to provide said second fluid under pressure to said plural tubes.

7. The prosthesis of claim 6 wherein said expandable means comprises a bellows.

8. The prosthesis of claim 7 additionally comprising constricting means having said reservoirs disposed therebetween and arranged to compress said reservoirs in automatic response to the expansion of said bellows.

9. The prosthesis of claim 8 wherein said constricting means comprise plural moveable members connected to said bellows, each of said moveable members being located on one side of a respective reservoir, and plural stationary members, each of which is located on the opposite side of said reservoir.

10. The prosthesis of claim 9 wherein said plural moveable members comprise disk-like elements mounted at spaced locations along an elongated rod-like member, said rod-like member being connected to said bellows.

11. The prosthesis of claim 7 wherein said fluid comprises one of the class of freon fluorocarbons.

12. The prosthesis of claim 4 additionally comprising a hydraulic chamber of a first predetermined volume and having a hydraulic fluid therein, first moveable piston means coupled to said expandable means, fluid reservoir means coupled to said inflatable means, said fluid reservoir means being of a second predetermined volume and having said second fluid therein, said second volume being substantially greater than said first volume, second piston means coupled to said hydraulic chamber, said first piston means moving in response to the expansion of said expandable means to cause said hydraulic fluid to be expelled from said hydraulic chamber, whereupon said second piston means moves to cause said second fluid in said fluid reservoir means to be provided to said inflatable means to pressurize said inflatable means.

13. The prosthesis of claim 12 wherein said first piston means is arranged to move through a first predetermined length of said hydraulic chamber, and wherein said second piston means is arranged to move a second predetermined length through said fluid reservoir means in response to the movement of said first piston means, said second predetermined length being substantially greater than said first predetermined length.

14. The prosthesis of claim 12 wherein said hydraulic chamber is located adjacent said expandable means and wherein said fluid reservoir means is located between said hydraulic chamber and said inflatable means.

15. The prosthesis of claim 14 wherein said fluid reservoir means comprises an elongated cylindrical chamber extending along the longitudinal axis of said cylinder and including a central passageway extending a substantial distance therethrough, said second piston means comprising an elongated piston shaft and a piston head, said piston shaft extending through said passageway, said hydraulic chamber being in fluid communication with said central passageway, said piston head being located within said cylindrical chamber, whereupon the expulsion of said hydraulic fluid from said hydraulic chamber causes said second piston to move down said cylindrical chamber to force said second fluid into said inflatable means.

16. The prosthesis of claim 15 additionally comprising sealing means for preventing the leakage of said hydraulic fluid and said second fluid.

17. The prosthesis of claim 16 wherein said hydraulic fluid comprises a silicone liquid.

18. The prosthesis of claim 17 wherein said second fluid comprises a silicone liquid.

19. The prosthesis of claim 12 wherein said cylinder is an elongated member having a front portion for disposition in the distal portion of a patient's penis and a rear portion for disposition inside the proximal portion of said penis, said first portion of said cylinder being disposed intermediate said front and rear portions thereof and wherein said rear portion is rigid.

20. The prosthesis of claim 2, wherein said cylinder is an elongated member having a front portion for disposition in the distal portion of a patient's penis and a rear portion for disposition inside the proximal portion of said penis, said first portion of said cylinder being disposed intermediate said front and rear portions thereof.

21. The prosthesis of claim 20, wherein said rear portion is rigid.

22. The prosthesis of claim 20, wherein said rear portion includes means for facilitating the sizing of said rear end portion to configure said cylinder to the size of the penis in which it is to be implanted.

23. The prosthesis of claim 22, wherein said last mentioned means comprises a plurality of longitudinally disposed annular recesses.

24. The prosthesis of claim 20 wherein said fluid comprises one of the class of freon fluorocarbons.

25. The prosthesis of claim 2 wherein said energy applying means includes heat generating means located within said expandable means.

26. The prosthesis of claim 25 wherein said heat generating means comprises at least one moveable member adapted to generate friction-induced heat as a result of movement of the penis.

27. The prosthesis of claim 26 wherein said expandable means comprises a bellows.

28. The prosthesis of claim 1, wherein said expandable means comprises a chamber formed of a strong and tough, yet flexible, material.

29. The prosthesis of claim 28, wherein said expandable means comprises a corrugated bellows.

30. The prosthesis of claim 29, wherein said material of said chamber comprises titanium.

31. The prosthesis of claim 29, wherein said material of said chamber comprises nickel.

32. The prosthesis of claim 1, wherein said fluid is in said second volumetric state when its temperature exceeds approximately 38° C.

33. The prosthesis of claim 1 wherein said fluid comprises one of the class of freon fluorocarbons.

34. The prosthesis of claim 1 wherein said energy applying means includes means for applying heat energy to said fluid.

35. An implantable penile prosthesis comprising an elongated cylinder for disposition within the penis, said cylinder including a first portion adapted to move from a non-erect, flaccid state to an erect, rigid state upon being pressurized with a fluid, said prosthesis including actuating means comprising energy applying means and a first fluid, said first fluid being changeable from a first state occupying a first volume to a second state capable of occupying a second volume greater than said first volume upon the application of energy thereto by said energy applying means, said cylinder including a reservoir communicating with said first portion of said cylinder and a second fluid in said reservoir, means for preventing said first fluid from mixing with said second fluid and force transmitting means for forcing said second fluid into said first portion of the cylinder to move said first portion to an erect rigid state upon said first fluid changing from its first state to its second state, and said pressure in said first portion being relieved upon said first fluid changing from said second state to said first state to move said first portion to a non-erect, flaccid state, said energy applying means being operative for applying energy to said first fluid when an erection of said penis is desired and for ceasing to apply energy to said first fluid when it is desired to permit the penis to assume a non-erect, flaccid state.

* * * * *